United States Patent [19]

Nishiyama et al.

[11] Patent Number: 4,934,185
[45] Date of Patent: Jun. 19, 1990

[54] DEVICE FOR MEASURING ADHESIVE STRENGTH AND SHEAR STRENGTH OF COATED FILM

[75] Inventors: Ituo Nishiyama; Tetsuo Mitani; Masazi Kozono, all of Mitsubishi, Japan

[73] Assignee: Mitsubishi Denki Kabushiki Kaisha, Tokyo, Japan

[21] Appl. No.: 296,149

[22] Filed: Jan. 12, 1989

[30] Foreign Application Priority Data

Jan. 25, 1988 [JP] Japan .............................. 63-14961[U]
May 26, 1988 [JP] Japan ............................ 63-130577[U]

[51] Int. Cl.$^5$ .............................................. G01N 3/34
[52] U.S. Cl. ................................... 73/105 A; 73/827
[58] Field of Search ........................ 73/150 A, 150 R

[56] References Cited

U.S. PATENT DOCUMENTS 2,960,865 11/1960 Brown ............................... 73/150 A
3,548,652 12/1970 Beatty et al. ...................... 73/150 A

FOREIGN PATENT DOCUMENTS 1956098 5/1971 Fed. Rep. of Germany .
2336212 2/1975 Fed. Rep. of Germany .
2503892 8/1975 Fed. Rep. of Germany .
2514154 10/1976 Fed. Rep. of Germany .

OTHER PUBLICATIONS

"Measuring Coatings Adhesion", Paint and Varnish Production, Mar. 1970, Dr. W. K. Asbeck, pp. 23–30.

Primary Examiner—Daniel M. Yasich
Attorney, Agent, or Firm—Oblon, Spivak, McClelland, Maier & Neustadt

[57] ABSTRACT

A device for measuring the adhesive or shear strength of a coated film comprising: a fixed member which can be fixed on an object to be measured; a guide member fixed on the fixed member; a moving member which moves along the guide member in parallel with a measuring surface of the object to be measured; a cutting blade supporting member; a cutting blade mounted on one end part of the cutting blade supporting member and press-contacted on the measuring surface; a mechanism for adjusting the press-contacting force of the cutting blade onto the measuring surface; a mechanism for adjusting a pressure contacting angle of the cutting blade; and a pressure detector for detecting cutting resistance generated by the cutting blade. The device also comprises a vertical displacement detector for detecting a vertical displacement with respect to the measuring surface of the object to be measured.

8 Claims, 18 Drawing Sheets

(a)

- RAKE ANGLE 10°
- SHEAR ANGLE 45°
- $F_T = 0$

- RAKE ANGLE 20°
- SHEAR ANGLE 50°
- $F_T < 0$

- RAKE ANGLE 0°
- SHEAR ANGLE 40°
- $F_T > 0$

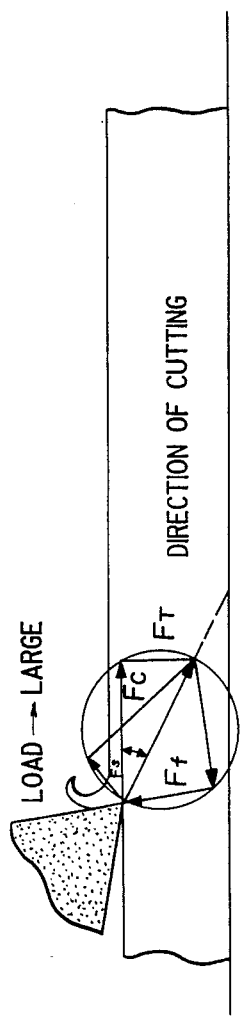
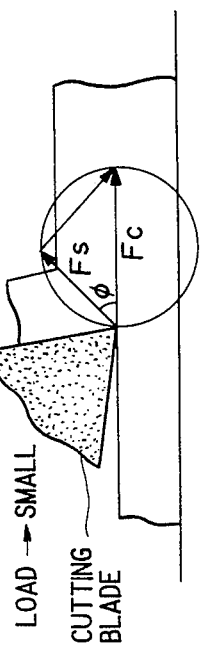
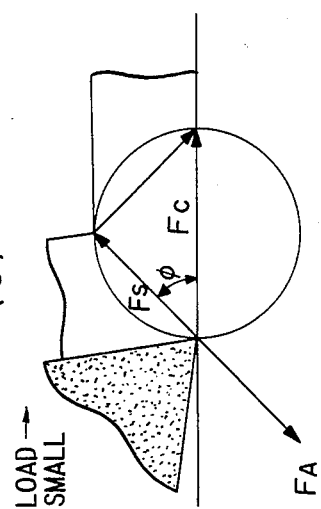
FIGURE 5 (a)
FIGURE 5 (b)
FIGURE 5 (c)

(a)

LOAD → LARGE

LOAD → SMALL $F_C$ = CUTTING FORCE (a)

(c)

(a)

(b)

(c)

DEVICE FOR MEASURING ADHESIVE STRENGTH AND SHEAR STRENGTH OF COATED FILM

BACKGROUND OF THE INVENTION

1. Field of the Invention

This invention relates to a device for measuring adhesive strength and shear strength of coated film, which makes quantitative measurement of the adhesive strength and shear strength of a film coated on an object so as to find out the basic properties of the film thus coated.

2. Discussion of Background

A conventional device for measuring adhesive strength of a coated film is as disclosed in, for example, Japanese Patent Application No. 178759/1986 invented by the present inventors and titled "Device for Measuring Adhesive Strength of Coated Film", the structure of which is as shown in FIG. 12 of the accompanying drawing.

In the drawing, a specimen mounting base (34) is fixed onto a sliding member (33) which is pivotally mounted on a guide shaft (32) immovably fastened to a support stand (31). A coated plate (35) to be a test specimen is mounted onto this specimen mounting base (34) by means of a specimen fixing implement (36). A screw-threaded rod (38) is screw-engaged in a nut (37) coupled to the specimen mounting base (34), one end part of which is connected with a motor (39). The sliding member (33) can be displaced linearly in the horizontal direction along the guide shaft (32), and slidingly moves on and along a guide shaft (41) fixed on the support stand (31) through a connecting member (40). The connecting member (43) fixed on the sliding member (42) is connected with another connecting member (45) fixed on another sliding member (44), whereby a guide shaft (46) causes the sliding member (44) to slide up and down. One end part of the guide shaft (46) constitutes a supporting body for a cutting blade (47), while the other end part thereof forms a screw-threaded rod where a thumb nut (48) for holding the cutting blade and a weight (49) are disposed. The weight (49) functions to adjust and establish the press-contacting force of the cutting blade (47) to the film coated plate (35). The front end part of a micrometer (50) fixed to the connecting member 45) is urged to the other connecting member (43) in a manner to cause the front end part of the cutting blade (47) to be in parallel with the surface of the material as the test specimen.

A pressure detector (51) fixed on the connecting member (40) detects a repulsive force to be generated against the cutting blade (47) through the sliding member (42) and the connecting rod (52). Measured data are converted by means of an A/D converter (53), then the A/D-converted data are introduced as inputs into a personal computer (54) wherein they are subjected to waveform-processing with use of a Fourier transformation program, and finally the thus waveform-processed data are outputted in the form of Fourier spectra, power spectra, and a graph of self-correlation function. A temperature regulator (55) such as a thermo-module is used for adjusting a temperature of the test specimen.

A coated plate having, for example, a length of 150 mm, a width of 70 mm, and a thickness of 1 mm was used as the test specimen (35) and a part of the coated film was peeled off in a size of 2 cm square to expose the surface of the base material. This partially exposed coated plate (35) was mounted on the specimen mounting base (34) by means of the specimen fixing implement (36) in such a manner that it may be tightly attached to the base, and then the cutting blade (47) having a blade width of 4 mm was applied onto the exposed part of the coated plate (35) and pushed against the coated plate by means of the weight (49) so that a pressing force of 600 g may be exerted to it. Then, adjustment is made by a micrometer (50) to bring the edge of the cutting blade (47) to be in parallel with the surface of the test specimen.

Then, an electric motor is driven to shift the coated plate (35) at a velocity of 1 mm/min., while detecting by means of the pressure detector (51) an interfacial cutting resistance to the cutting blade (47) which has been transmitted to it through the connecting rod (52) fixed to the sliding member (42). First of all, a part of the base material is cut in 5 mm length, followed by cutting a part of the coated film in 15 mm length. Then, by use of the thermo-module (55), the temperature of the coated plate is regulated to a constant temperature level ranging from −10° C. to 60° C.

FIG. 13 of the accompanying drawing is a characteristic diagram showing the cutting resistance to the cutting blade at the interface between the base material and the coated film, wherein the ordinate axis denotes the cutting resistance (kg) at an interface between the coated layer and the base material, and the abscissa axis represents a cutting length (mm) of the interface between the coated film and the base material. As seen from this characteristic diagram, the measured data appear in the waveform, in which "A" indicates the cutting resistance of the surface of the base material, and "B" indicates the cutting resistance of the interface between the coated film and the base material.

FIGS. 14(a), 14(b) and 14(c) are graphical representations corresponding to FIG. 13 above, respectively showing the cutting resistance at the interface in case the conditions for the surface treatment of the base material are varied for coating an epoxy type film by electrical deposition, in which FIG. 14(a) is the characteristic diagram of the interfacial cutting resistance of the test specimen which has been subjected to the surface preparation of the base material with use of zinc phosphate in acicular crystal; FIG. 14(b) is the characteristic diagram of the interfacial cutting resistance of the test specimen which has been subjected to the surface preparation of the base material with use of zinc phosphate in columnar crystal; and FIG. 14(c) is the characteristic diagram of the interfacial cutting resistance of the test specimen which has been subjected to the surface preparation of the base material with use of zinc phosphate in scaly crystal. It will be seen from these characteristic diagrams that, even when the coated film is of the same material, if the formation treatment of the treated steel plate differs, the adhesive strength of the coated film differs accordingly with the consequence that the interfacial cutting resistance and the waveform become varied, as shown in FIGS. 14(a), 14(b) and 14(c).

FIG. 15 is a flow chart for the wave form analysis program, in which the measured data (55) of the interfacial cutting resistance is processed by the A/D converter (56), inputted into the personal computer (57), and outputted to a program file (58). After producing the output data of the program file (58) in the form of a graph, a processing range is inputted by a cursor from the image plane, followed by processing (60) the measured data by use of the subsequent Fourier conversion program (59) to output the result of conversion into the file.

Then, the inputs are introduced into the respective files of Fourier spectra, power spectra and self-correlation function, from which graphs are outputted (61).

FIG. 16 is a power spectral diagram to be obtained by the Fourier conversion of the interfacial cutting resistance of a urethane type coating material for each heating time of zero hr., 100 hrs., 300 hrs., and 650 hrs.. In this graphical representation, the abscissa represents the number of vibration (cps) and the ordinate denotes power spectrum ($cm^2/sec^3$). From this graph, it will be seen that, in the heat-resistance test at 160° C., the power spectrum tends to lower while the peak number of vibration tends to increase as the heating time becomes prolonged.

The interfacial cutting resistance is a composite force of the adhesive strength of the coated film and the material strength, the breaking form of which is recorded as a waveform. By subjecting the measured values of the interfacial cutting resistance to the Fourier conversion and then carrying out the waveform analysis, there can be obtained information for clarifying the nature of the phenomenon.

By the way, in the above-described conventional device for measuring the adhesive strength of the coated film, explanations have been made as to an instance of using a general coated plate having a film thickness of a few tens of micrometers or above. It may, however, be feasible that film be coated on a plastic plate to obtain the same effect as in the above-mentioned conventional example.

On account of such construction of the conventional device for measuring the adhesive strength of the coated film as described above, it was necessary to provide the coated plate (35) for the film testing purpose and to analogize the adhesive strength of the coated film of the object to be tested on the basis of this result of measurement, hence there remained problems in respect of reliability and precision of the result of measurement (or analogy).

There was also a problem such that the conventional device is able to find out variations in the adhesive strength of the coated film only indirectly by the waveform analysis due to the cutting force and the Fourier conversion from the resulted waveform, and no adhesive strength and the shear strength can be found out directly.

SUMMARY OF THE INVENTION

The present invention has been made with a view to solving these problems as mentioned above, and aims at providing a device which is capable of measuring the adhesive strength or shear strength of a film coated not only on a test specimen for measurement, but also on an actual product at the working site, and which is also capable of measuring the adhesive strength or the shear strength of each and every layer of coated film constituting a multi-layered coating.

In addition to the above mentioned purpose, it is also an object of the present invention to provide a device which is capable of detecting the cutting resistance simultaneously with detection of its measuring position.

According to the present invention, in general aspect of it, there is provided a device for measuring adhesive strength or shear strength of a coated film, which comprises in combination: a fixed member which can be fixed on an object to be measured; a guide member fixed on said fixed member; moving member which moves linearly on and along said guide member in parallel with a measuring surface of said object to be inspected; a cutting blade supporting member which displaces linearly in parallel with the measuring surface of said object to be inspected in association with said moving member and which is linearly displaceable in the direction perpendicular to said measuring surface; a cutting blade mounted on one end part of said cutting blade supporting member and press-contacted on said measuring surface; means for adjusting the press-contacting force of said cutting blade onto said measuring surface, said adjusting means being disposed at the other end part of said cutting blade supporting member; means for adjusting the press-contacting angle of said cutting blade; a pressure detector for detecting cutting resistance to be generated in said cutting blade; and means for recording an output from said pressure detector.

According to the present invention, in another aspect of it, there is provided a device for measuring adhesive strength or shear strength of a coated film, which comprises, in addition to the above-mentioned constituent elements, a vertical displacement detector for detecting a vertical displacement quantity of the cutting blade with respect to the measuring surface of said object to be measured; and means for recording an output from this vertical displacement detector.

The foregoing objects, other objects as well as specific construction and operations of the measuring device for adhesive strength or shear strength of a coated film according to the present invention will become more apparent and understandable from the following detailed description thereof, when read in conjunction with the accompanying drawing.

DETAILED DESCRIPTION OF THE PREFERRED EMBODIMENTS

In the following, the present invention will be described in specific details in reference to the accompanying drawing.

The measuring device for adhesive strength or shear strength of a coated film according to the present invention is fixed to an object to be measured by means of a fixed member, and a cutting blade is caused to move in parallel with the measuring surface of the object to be measured, while press-contacting the blade onto the measuring surface of the object, and cutting resistance to be generated in the cutting blade is detected and recorded, whereby the adhesive strength or shear strength of the coating film on the object to be measured can be directly found out.

Also, according to another aspect of the present invention, since the cutting position of the cutting blade (a displacement of the cutting blade in the direction of its cutting depth) can be detected simultaneously with detection of the cutting resistance, so that there is no necessity for detecting the film thickness. Further, since no difference between the cutting resistance and the measuring position takes place, the adhesive strength or shear strength of the coated film can be measured easily and with high precision.

With a view to enable those persons skilled in the art to put this invention into practice, the following preferred embodiment will be explained in reference to the accompanying drawing.

Figure 1:
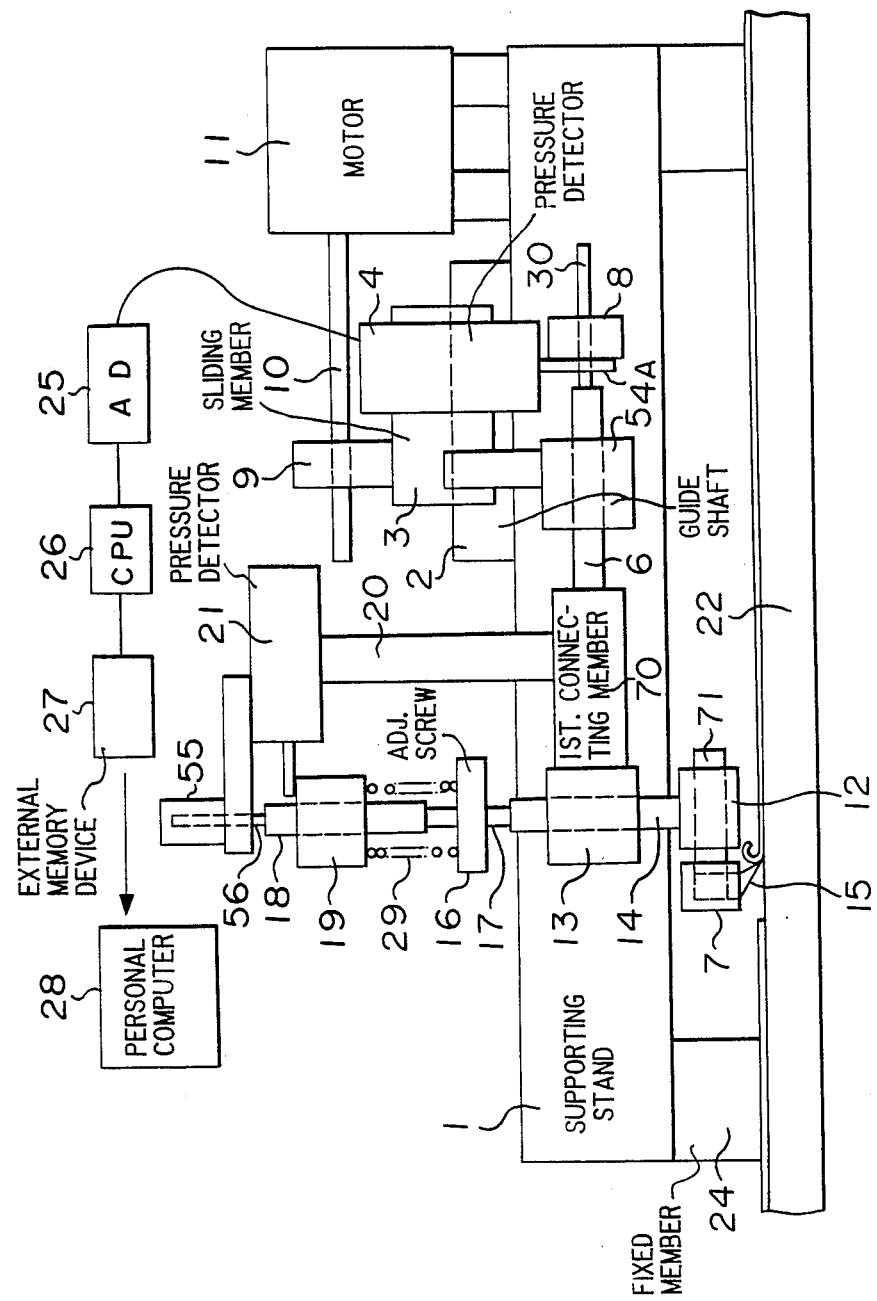
FIG. 1 is a schematic diagram in front view showing a general construction of the measuring device for adhesive strength or shear strength of a coated film according to one embodiment of the present invention.
Figure 2:
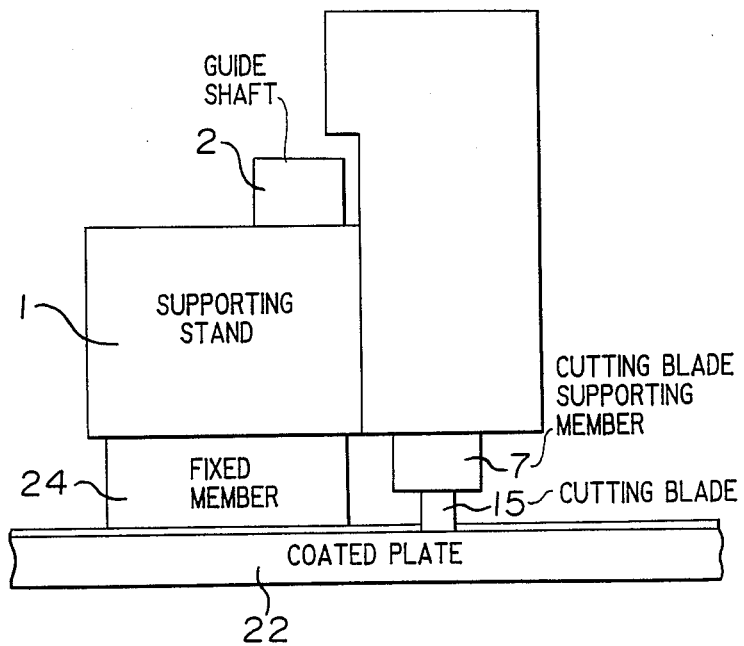
FIG. 2 is a side view of the measuring device shown in FIG. 1.

Referring first to FIG. 1 which is a front view showing a structure of the device for measuring adhesive strength or shear strength of coated film according to one embodiment of the present invention, and FIG. 2 which is a side view of the device, a supporting stand (1) is fixed to a coated plate (22) as an object to be measured by means of a fixed member (24) such as a magnet, and a guide member or a guide shaft (2) is fixed to the magnet (24) through the supporting stand (1). A pressure detector (4) and a guide shaft (5) are fixed onto a moving member or sliding member (3), while a sliding member (6) is pivotally mounted on the guide shaft (5). At one end part of this sliding member (6), there is fixed a first connecting member (70), while, at the other end part thereof, there is fixed a screw-threaded connecting rod (30). In this connecting rod (30), there is screw-engaged a receiving member (8) which can be fixed at an arbitrary position. A screw-threaded rod (10) is screwed into a nut (9) which is connected with the sliding member (3), one end of which is connected with a motor (11). The sliding member (3) is linearly displaceable in parallel with the measuring surface (i.e., in the left-and-right direction as viewed from the top surface of the drawing) of the coated plate (22) on and along the guide shaft (2). When the sliding member (13) moves in the left-and-right direction in association with the sliding member (3), the cutting blade (15) fixed on the cutting blade supporting member (7) also moves in the left-and-right direction. With driving of the motor (11), the pressure detector (4) fixed on the sliding member (3) moves linearly on and along the guide shaft (2). A pressure sensing member (4A) is projectively provided on the pressure detector (4), which functions to push the receiving member (8) in the right direction as viewed from the top surface of the drawing. Since the receiving member (8) is fixed on the sliding member (6) through the connecting rod (30), the sliding member (6) moves in the right direction as viewed from the top surface, of the drawing. The guide shaft (5) plays a role of maintaining the sliding member (6) in parallel with the measuring surface of the object to be inspected (22) and transmitting the cutting resistance to be generated in the cutting blade (15) to the pressure sensing member (4A). In other words, since the guide shaft (5), the pressure detector (4), and the sliding member (3) are mutually fixed to move together, only the cutting resistance of the cutting blade (15) is transmitted to the pressure sensing member (4A) without the sliding frictional force of the guide shaft (5) and the sliding member (6) being applied thereto. Force which acts on the pressure sensing member (4A) is detected by the pressure detector (4).

In the next place, brief explanations will be given as to the vertical movement of the cutting blade (15) with respect to the measuring surface of the object to be inspected (22), which is described in unexamined Japanese Patent Publication No. 169745/1986 of the same applicant as that of the present application. The guide shaft (14) is pivotally mounted on the sliding member (13) in a manner to be slidable up and down. At one end of the guide shaft (14), there is provided the support member (7) for the cutting blade (15), while, at the other end of the guide shaft there is fixed the screw-threaded rod (17), into which an adjusting screw (16) having a control lug constituting an adjusting means for the press-contacting force is screwed. The screw threaded rod (17) has the guide shaft (18) fixed at its one end, while the sliding member (19) is pivotally mounted on the guide shaft (18). The pressure detector (21) held on the pressure detector supporting table (20) which is fastened to a first connecting member (70) functions to detect, through the guide shaft (14), the screw-threaded rod (17) and the guide shaft (18), a repulsive force to be generated in the cutting blade (15) in the direction vertical to the measuring surface of the coated plate (i.e., in the direction vertical to the measuring surface of the drawing). The press-contacting force of the cutting blade (15) to the measuring surface of the coated plate (22) is adjusted while monitoring the detected value. In more detail, a spring (29) is disposed between the adjusting screw (16) with control lug and the sliding member (19), and the press-contacting force of the cutting blade (15) to the coated plate (22) is adjusted for appropriate value with the adjusting screw (16) with control lug. Also, another guide shaft (71) is rotatably mounted on the sliding member (12) which is connected to the guide shaft (14), while the supporting member (7) is fixed at one end part of the guide shaft (71). Both sliding member (12) and the guide shaft (71) constitute a press-contacting angle adjusting means. By rotating the guide shaft (71), adjustment is made such that the edge of the cutting blade (15) may come into close contact with the coated film surface on the coated plate (22). The vertical displacement detector fixed on the pressure detector (21), i.e., a differential transducer (55), detects movements of a rod (56) connected to the end part of the guide shaft (18) to thereby detect a vertical displacement of the cutting blade (15) with respect to the measuring surface of the coated plate (22), i.e., displacement of the cutting blade (15) in the direction of its depth of cutting.

The data as measured by the pressure detector (4) and the differential tranducer (55) are subjected to A/D-conversion by the A/D converter (25), then to arithmetic operation by a 16-bit CPU (26), for example, and are finally sorted in an external memory device (27). The data as stored in the external memory device (27) are introduced as inputs into a personal computer (28), wherein the adhesive strength or the shear strength of the coated film is calculated with a calculation program, and the waveform processing is effected with a Fourier conversion program, from which graphs of the Fourier spectrum, the power spectrum and the self-correlation function are produced as outputs. With the above-mentioned construction, use is made, as an object to be measured, of a column of an iron bridge, on which paint has been coated with a width of 30 cm and a length of 10 m, for example, and then the cutting blade (15) is fixed on the iron column with the magnet (24) so that it may be positioned on one part of the coated film. The cutting blade (15) having a width of 4 mm and a rake angle of 10 degrees is applied onto the surface of the coated film of the coated plate (22) and pressed by the adjusting screw (16) with control lug in such a manner that 2 kg of pressing force may be impressed upon it.

Figure 3:
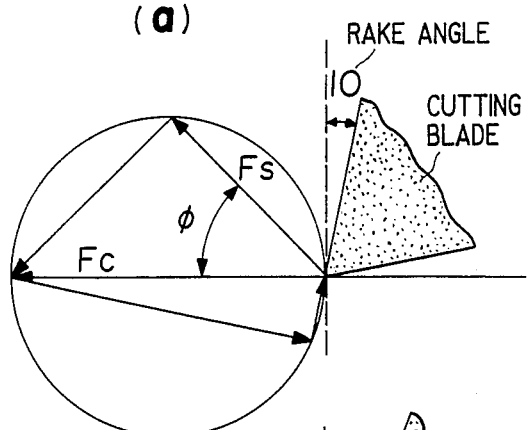
FIG. 3(a), 3(b) and 3(c) are respectively explanatory diagrams indicating a relationship between a rake angle and a cutting vector of the cutting blade according to the present invention.
Figure 3B:
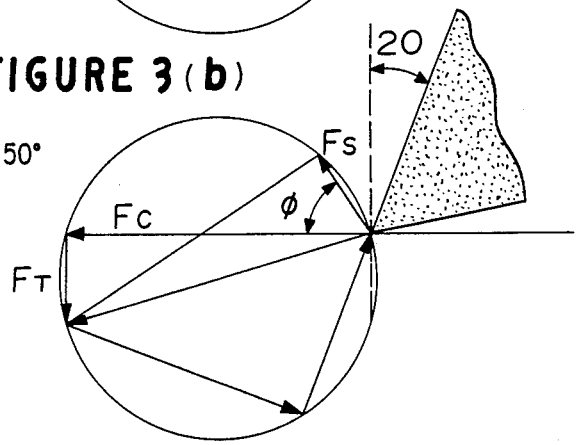
Figure 3C:
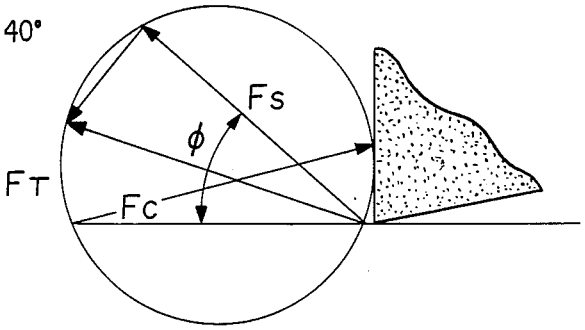

FIGS. 3(a), 3(b) and 3(c) are respectively explanatory diagrams showing the relationship between the rake angle and the cutting vector of the cutting blade (15) with no load on it, wherein FIG. 3(a) indicates a case of 10 degrees of the rake angle, FIG. 3(b) is a case of 20 degrees of the rake angle, and FIG. 3(c) is a case of 0 degrees of the rake angle. Considering these cases, the following equations are established from the balancing relationship of force.

$$F_C = \lambda A_0 (1 + \cot\Phi) \quad (1)$$

$$F_T = \lambda A_0 (\cot\Phi - 1) \quad (2)$$

(where: λ denotes the shear strength of the coated film (kg/cm$^2$); $A_0$ represents the cutting area (cm$^2$); and Φ indicates the shear angle)

In the case of no load being applied to the cutting blade, if cotΦ is greater than 1 (cotΦ>1) in the above equation (2), $F_T$ is greater than zero ($F_T > 0$), whereby the cutting blade is pushed up; on the contrary, if cotΦ is smaller than 1 (cotΦ<1), $F_T$ is smaller than zero ($F_T < 0$), whereby the cutting blade cuts into the coated layer. Accordingly, if the relationship is established in such a manner that cotΦ may be equal to 1 (cotΦ=1), the value of Φ being variable depending on the rake angle α of the cutting blade, the cutting blade (15) no longer moves up and down during the cutting operation, whereby it can stay at a predetermined depth.

Figure 4:
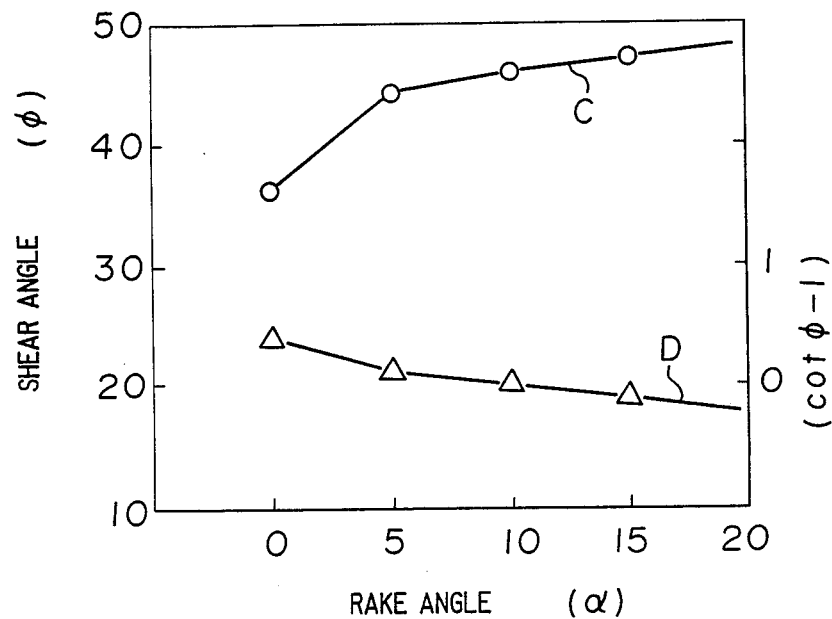
FIG. 4 is a characteristic diagram showing one example of a relationship between a rake angle and a shear angle (cot Φ-1) of the cutting blade according to the present invention.

FIG. 4 is a diagram showing a relationship among the rake angle (α) of the cutting blade, its shear angle (Φ), and (cotΦ−1), in which the ordinate axis denotes the shear angle (Φ) and (cotΦ−1), and the abscissa axis represents the rake angle (α). In this graphical representation, the characteristic curve (C) denotes a relationship between the rake angle and the shear angle, while the characteristic curve (D) indicates a relationship between the rake angle and (cotΦ−1). It will be seen from this characteristic diagram that the shear angle, at which the value of $F_T$ becomes zero, is 45 degrees, and the rake angle at that time is 10 degrees. Since this relationship differs to some extent depending on the material to be cut, it is necessary that the shear angle be adjusted with a pressing load for the purpose of bringing the value of $F_T$ to zero.

When the motor (11) is driven to move the cutting blade (15) at a speed of 1 mm/min., while pressing it onto the surface of the coated film under a pressing force of 2 kg, the blade (15) cuts into the coated film. During the cutting, when the load is adjusted, the cutting blade is brought to its balanced state and no longer moves up and down, as mentioned above. For instance, if the load is adjusted at a position where the cutting blade has reached an interlayer section, the cutting blade takes a balance to cut the interlayer section; on the other hand, if the load is adjusted at a position where the cutting blade has reached an interface section, the cutting blade takes a balance to cut the interface section. After measurement of one surface layer, the subsequent layer comes out, for which the same measurement can be done as mentioned above. In this way, the measurement can be done sequentially starting from the surface layer to the subsequent under layers with the result that the properties of each individual layer in a multi-layered coating can be measured easily.

The cutting resistance force of the cutting blade (15), which has been transmitted through the connecting rod (30) fixed on the sliding member (6), is detected by the pressure detector (4), and the vertical displacement (displacement in the direction of depth of the coated film) is detected by the differential transducer (55). Then, these detected values are stored in the external memory device (27) such as FDD, etc. By subjecting the data as stored in the external memory device (27) to the computation and waveform processings, it is possible to measure the adhesive strength or the shear strength of the coated film.

FIGS. 5(a) to 5(d) are analytical diagrams, each showing diagrammatic interpretation of the data to be obtained by the above-described measurement. The cutting blade is placed on the surface of the coated film and caused to cut into the coated film under a high pressing load along a dotted line with a cutting angle of approximately 3 degrees (FIG. 5(a)). At a position where the cutting blade reaches the interfacial section, when the pressing load is adjusted, the cutting blade moves on and along the interfacial section (FIG. 5(c)). In a state of the cutting blade moving in the direction of depth under a high pressing load (i.e., the value $F_T$ is generated), the value $F_C$ contains therein a value $F_C'$, because of a frictional force $\mu$ to be generated in the edge of the cutting blade due to the degree of its sharpness and the cutting property of the material used. For obtaining this value of $F_C$, it may be sufficient to measure the value by varying the pressing load, whereby the relationship between the pressing load and the force in the $F_C$ direction generated by such pressing load is established as shown in the characteristic diagram of FIG. 6. In this graphical representation, the ordinate represents magnification of the value $F_C$ and the abscissa denotes the pressing load during the cutting. From this graphical representation, the true force F in the direction of $F_C$ is represented as follows:

$$F = F_C/(0.2W+1) \quad (3).$$

From the equation (1), the shear strength is represented as follows:

$$\lambda = F_C/(0.2W+1)A_0(1+\cot\Phi) \quad (4).$$

(where: $A_0$ represents "width of cutting blade (W) × film thickness (d)"; and W denotes the pressing load (kg))

Figure 5:
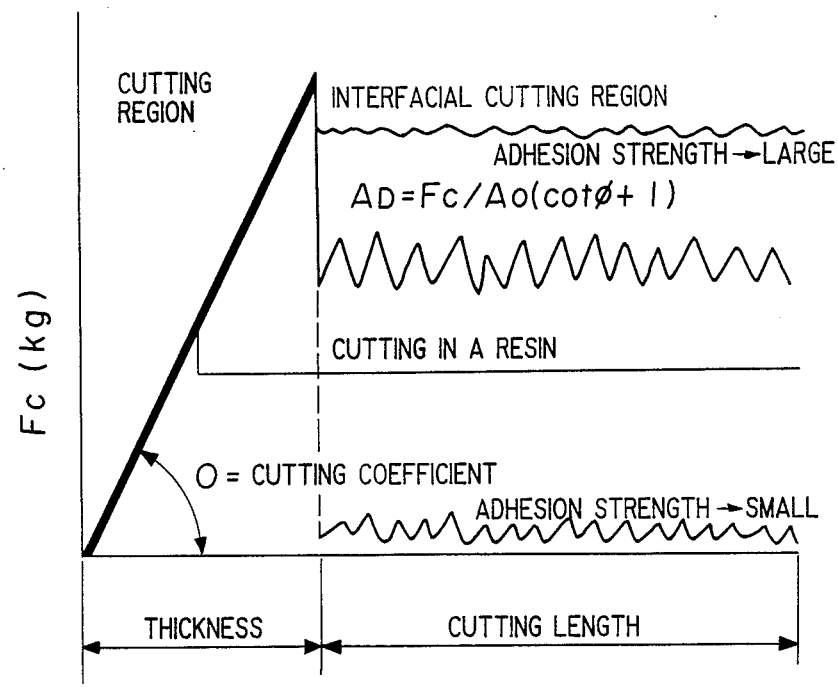
FIGS. 5(a), 5(b), 5(c) and 5(d) are respectively explanatory diagrams for analysis of data to be obtained from this first embodiment of the present invention.
Figure 6:
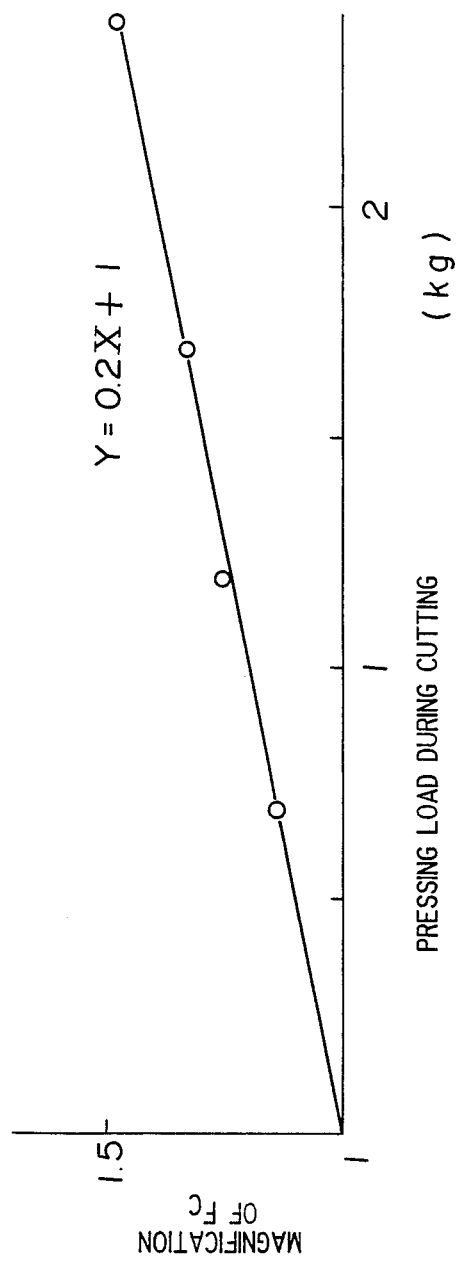
FIG. 6 is a characteristic diagram showing a relationship between a pressing load of the cutting blade and a force in the direction of $F_C$ to be generated by the pressing load.
Figure 7:
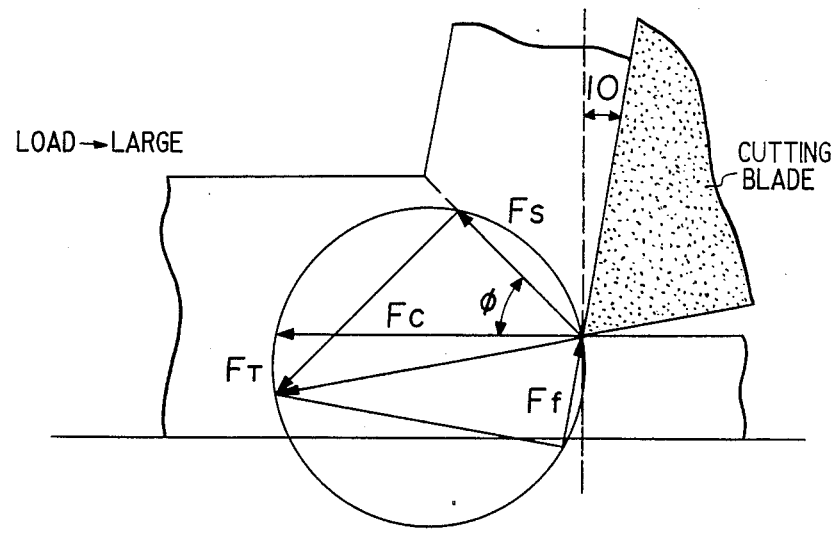
FIGS. 7(a) and 7(b) are respectively explanatory diagrams showing a relationship between a pressing load and a cutting vector of the cutting blade.
Figure 7:
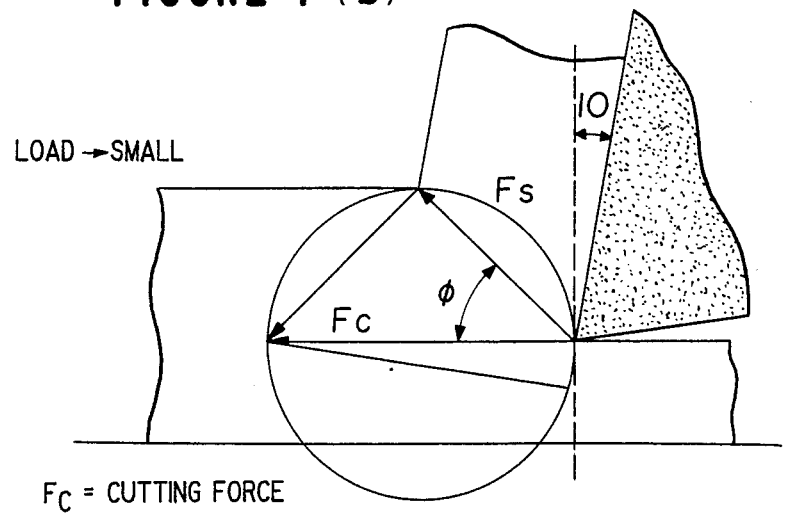

FIGS. 7(a) and 7(b) are respectively explanatory diagrams showing a relationship between the pressing load and the cutting vector of the cutting blade. FIG. 7(a) shows the cutting vector during the cutting operation by the blade, and FIG. 7(b) shows the cutting vector in the state of the value $F_T$ having been made zero by adjustment of the pressing load, in which case F is equal to $F_C$ (F=$F_C$). It is also possible to find out the shear force $\lambda$ from the values of both $F_C$ and in this state (the value $F_C$ does not contain therein the frictional force to be generated at the time of the cutting). FIG. 5(d) is a graph to be obtained by the method of measurement according to the present invention, in which the cutting force $F_C$ with respect to the value d in the thickness direction of the cutting blade is represented by the graph. In this graphical representation, the ordinate axis denotes the cutting force $F_C$ and the abscissa axis denotes the thickness of the cutting blade and the cutting length. Inclination $\Phi$ of the cutting blade depends upon hardness of the material used. The adhesive strength $A_D$ of the coated film can be found out of the value $F_C$ in the state of the cutting blade having reached the interfacial section and the value $F_T$ having been made zero by adjustment of the pressing load. That is to say, the adhesive force $F_A$ acts in the state of opposing the cutting vector $F_S$ of the edge of the cutting blade, as shown in FIG. 5(c). Therefore, the adhesive strength $A_D$ is represented as follows, provided however that, when the value $F_T$ is Smaller than zero (see FIG. 10), the frictional force to arise from cutting of the material surface should be deducted:

$$A_D = F_C/A_0(1+\cot\Phi) \quad (5)$$

Figure 8:
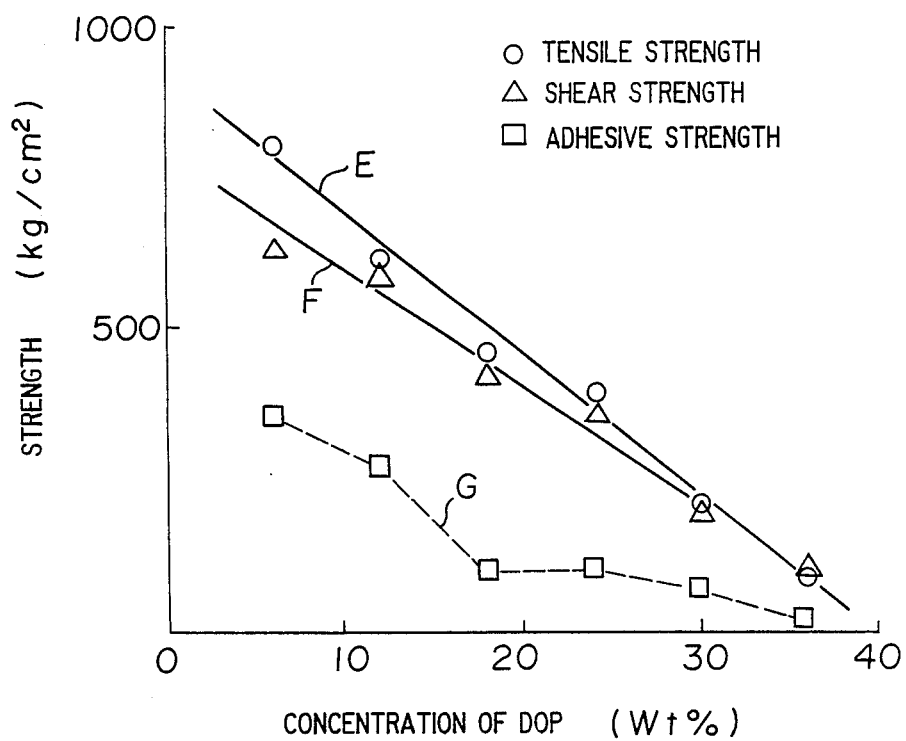
FIG. 8 is a characteristic diagram showing influence of DOP (dioctyl phthalate) concentration on each of the shear strength and adhesive strength of nitro-cellulose lacquer coated film, hereinafter NC lacquer coated film as measured by this embodiment of the present invention, along with tensile strength of the coated film according to a comparative example.
Figure 9:
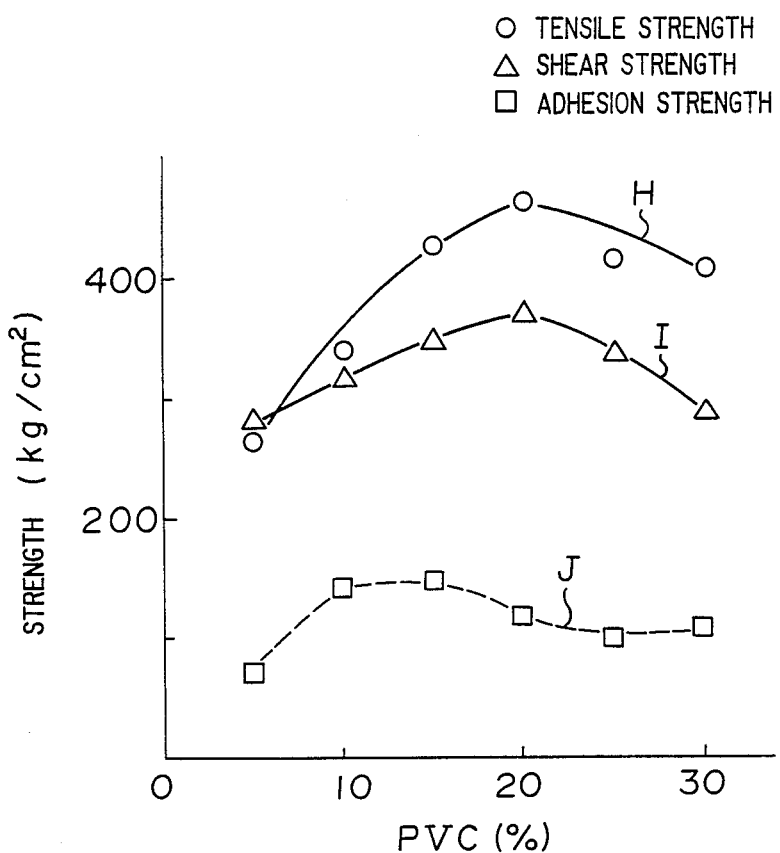
FIG. 9 is a characteristic diagram showing influence of PVC on each of the shear strength and adhesive strength of NC lacquer coated film, along with tensile strength of the coated film according to a comparative example.

FIGS. 8 and 9 are respectively graphical representations indicating, for the purpose of verifying propriety of the data to be obtained from the measurement by the method according to the present invention, the results of measurement (adhesive strength and shear strength) done by the device of this embodiment, using a coated film of known physical properties (with its tensile strength having been found out by use of a separated film), along with tensile strength of separated coated film. FIG. 8 is a characteristic diagram showing the influence of DOP (dioctyl phthalate) concentration on each of the tensile strength, shear strength and the adhesive strength of NC lacquer coated film, wherein the ordinate axis denotes the strength (kg/cm$^2$) and the abscissa axis represents concentration of DOP (wt %). FIG. 9 is a characteristic diagram showing the influence of PVC (polyvinyl chloride) (volume concentration of pigment (TiO$_2$) on each of the tensile strength, shear strength and the adhesive strength of NC lacquer coated film, wherein the ordinate axis denotes the strength (kg/cm$^2$) and the abscissa axis represents concentration of PVC (%).

In these graphs, the characteristic curve E denotes influence of the DOP concentration on the tensile strength of the NC lacquer coated film; the characteristic curve F indicates influence of the DOP concentration on the shear strength of the same coated film; the characteristic curve G represents influence of the DOP concentration on the adhesive strength of the same coated film; the characteristic curve H denotes influence of the PVC on the tensile strength of the NC lacquer coated film; the characteristic curve I indicates influence on the shear strength of the same coated film; and the characteristic curve J represents influence of the PVC concentration on the adhesive strength of the same coated film. In respect of comparison of the tensile strength of the separated coated film and the shear strength of the interfacial cutting method, the respective methods of measurement as in FIGS. 8 and 9 differ from each other in point of the state of presence of the coated film per se or the method of measurement with the consequence that the measured values do not become coincident (in general, test specimens under the same conditions indicate their shear strength which is about 1.5 times as high as that of the tensile strength). On account of the rake angle of the cutting blade used in this test being 20 degrees, its shear angle $\theta$ changs to some extent from 45 degrees, the angular difference of which is also included in this factor of non-coincidence.

Figure 10:
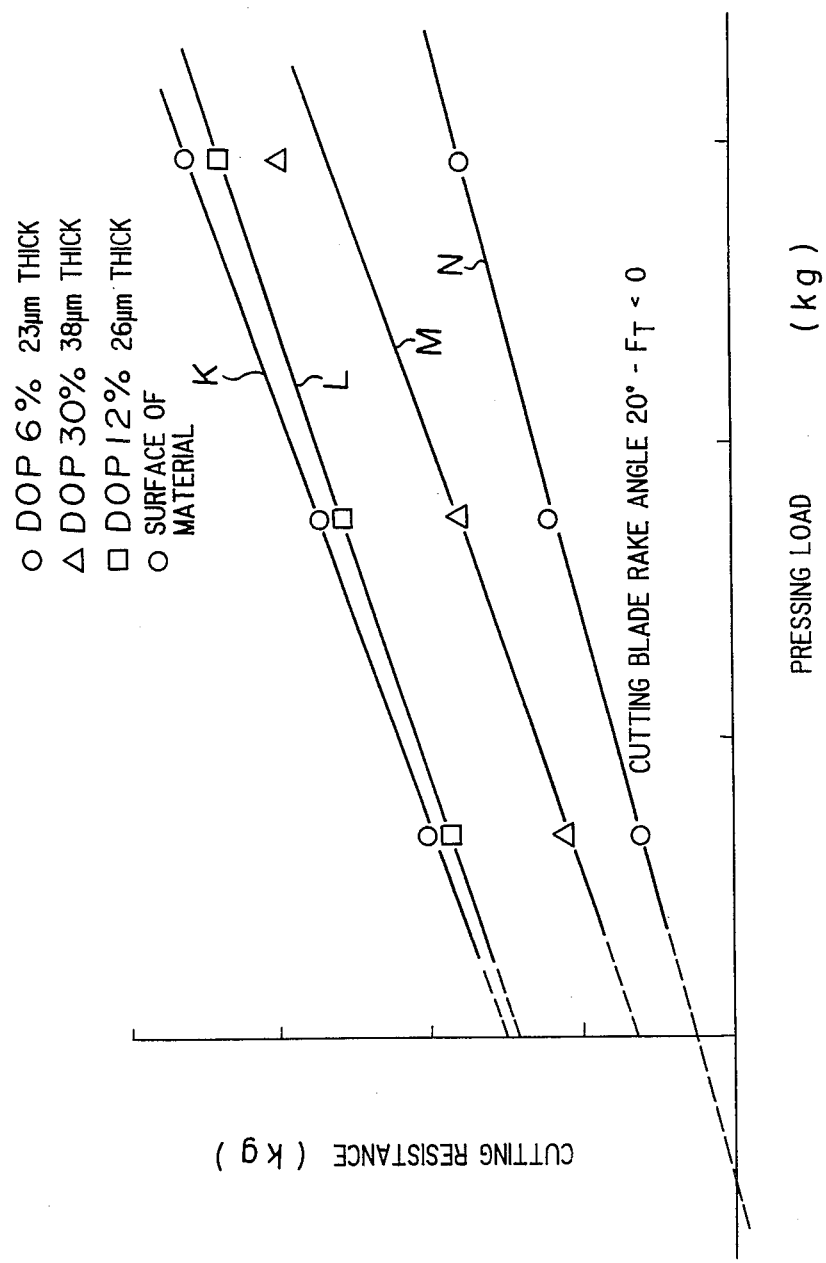
FIG. 10 is a characteristic diagram showing a relationship between the pressing load and the cutting resistance.

FIG. 10 is a graphical representation showing a relationship between the pressing load at the rake angle of 20 degrees and the cutting resistance on the surface of the coated film and the material used, in which the ordinate axis represents the cutting resistance (kg) and the abscissa axis denotes the pressing load (kg). In the graph, the characteristic curve K shows the relationship of the NC lacquer coated film of 23 $\mu$m (DOP concentration of 6%) with the cutting resistance and the pressing load; the characteristic curve L indicates the relationship of the NC lacquer coated film of 26 $\mu$m (DOP concentration of 12%) with the cutting resistance and the pressing load; the characteristic curve M denotes the relationship of the NC lacquer coated film of 38 $\mu$m (DOP concentration of 30%) with the cutting resistance and the pressing load; and the characteristic curve N indicates the relationship of the surface of the material with the cutting resistance and the pressing load. In the computation of the adhesive strength, 0.7 kg is to be deducted from the cutting force $F_C$ of the coated film, when $F_C$ is smaller than zero ($F_C<0$) and the pressing load is 1 kg. Such deduction becomes unnecessary when $F_T$ is set to be equal to zero ($F_T=0$). The measured results of the coated films of known physical properties as shown in FIGS. 8 and 9 indicate that both are coincident in their trend.

Figure 11:
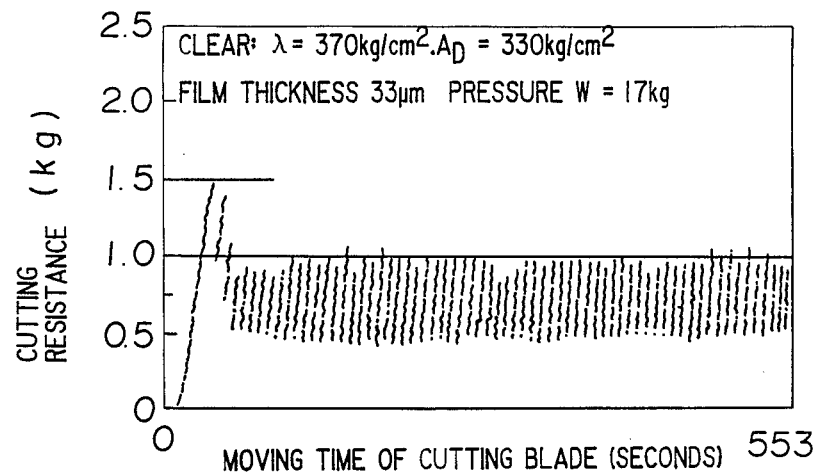
FIGS. 11(a), 11(b), 11(c) and 11(d) are respectively characteristic diagrams showing the cutting resistance of a four-layered coating.
Figure 11:
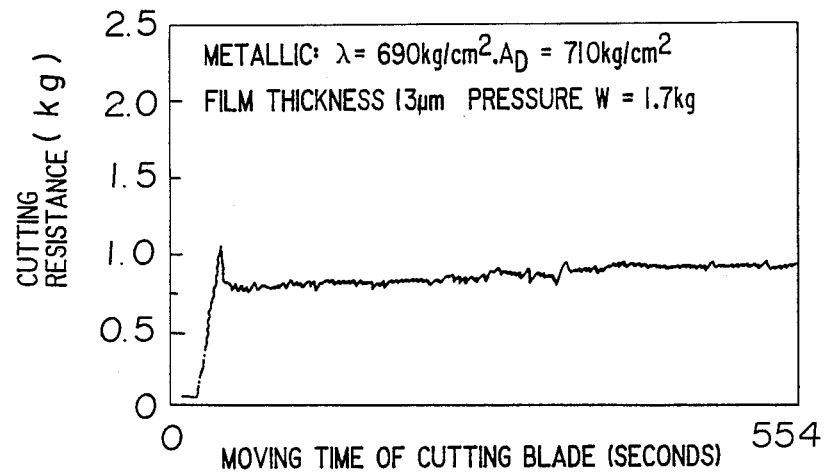
Figure 11:
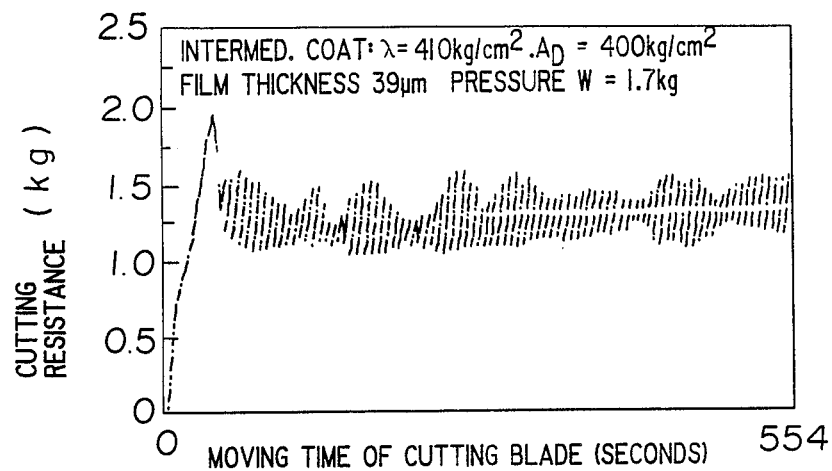
Figure 11:
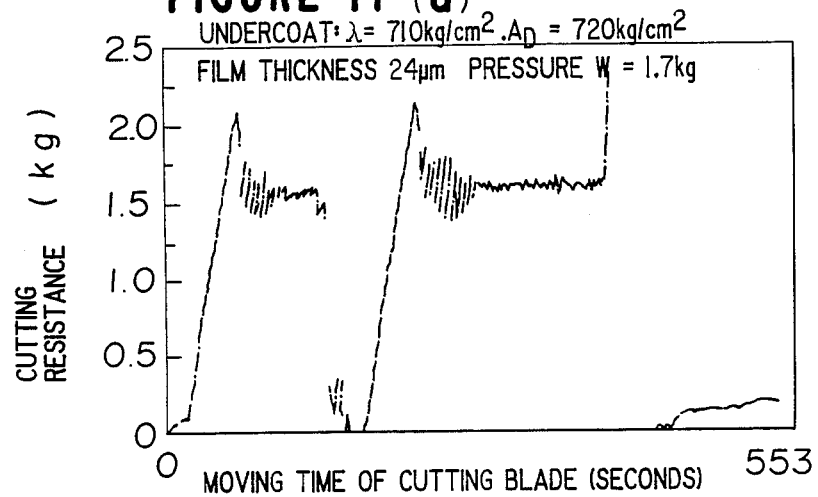
Figure 12:
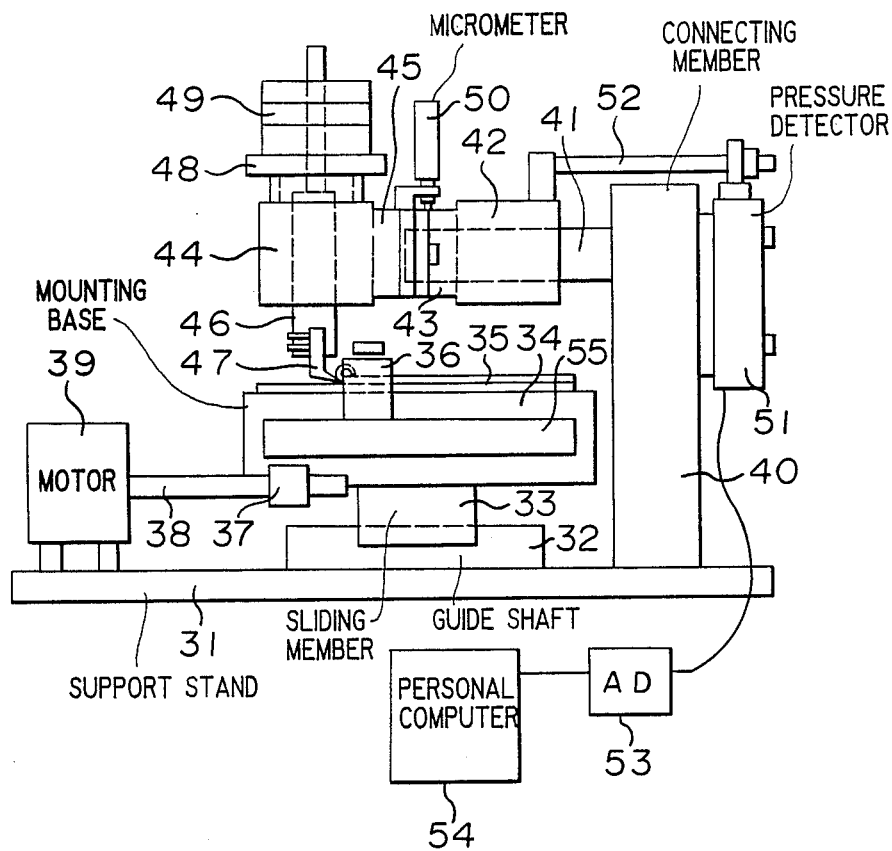
FIG. 12 is a schematic diagram showing a construction of a conventional device for measuring adhesive strength of a coated film.
Figure 13:
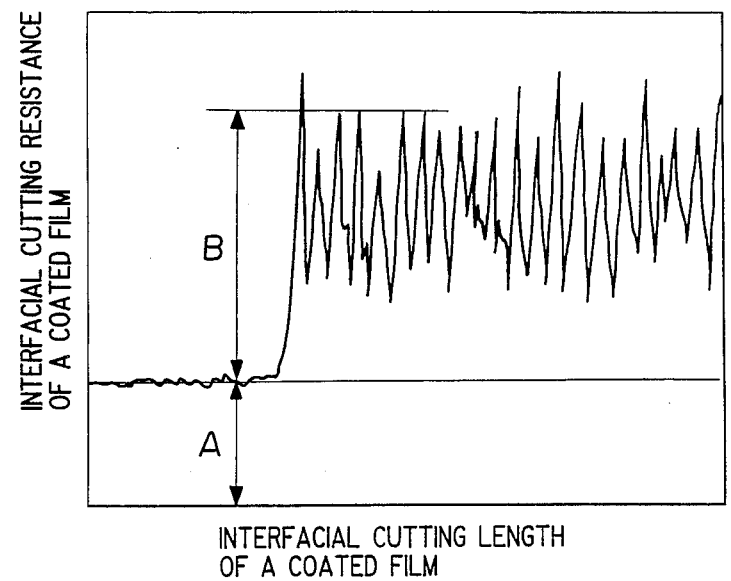
FIG. 13 is a characteristic diagram showing one example of an interfacial cutting length versus interfacial cutting resistance characteristic.
Figure 14:
FIGS. 14(a), 14(b) and 14(c) are respectively characteristic diagrams showing the interfacial cutting resistance of an epoxy type coating material for electrical deposition.
Figure 14:
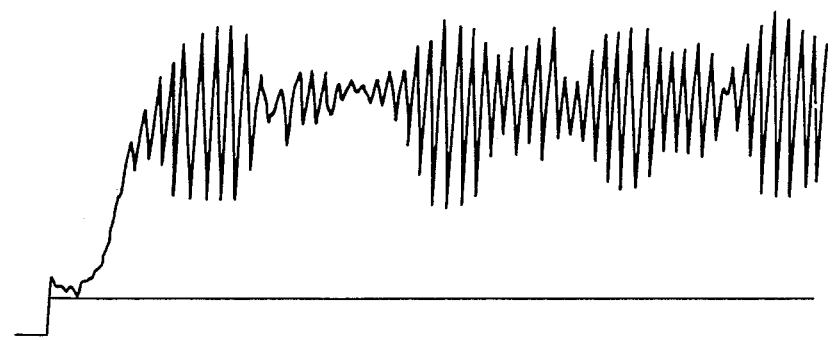
Figure 14:
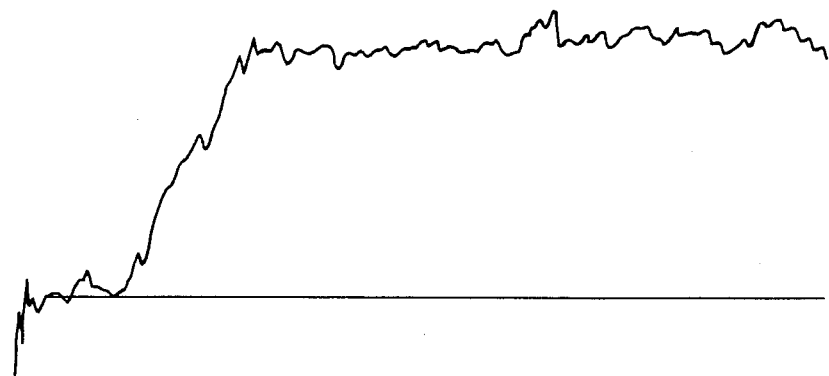
Figure 15:
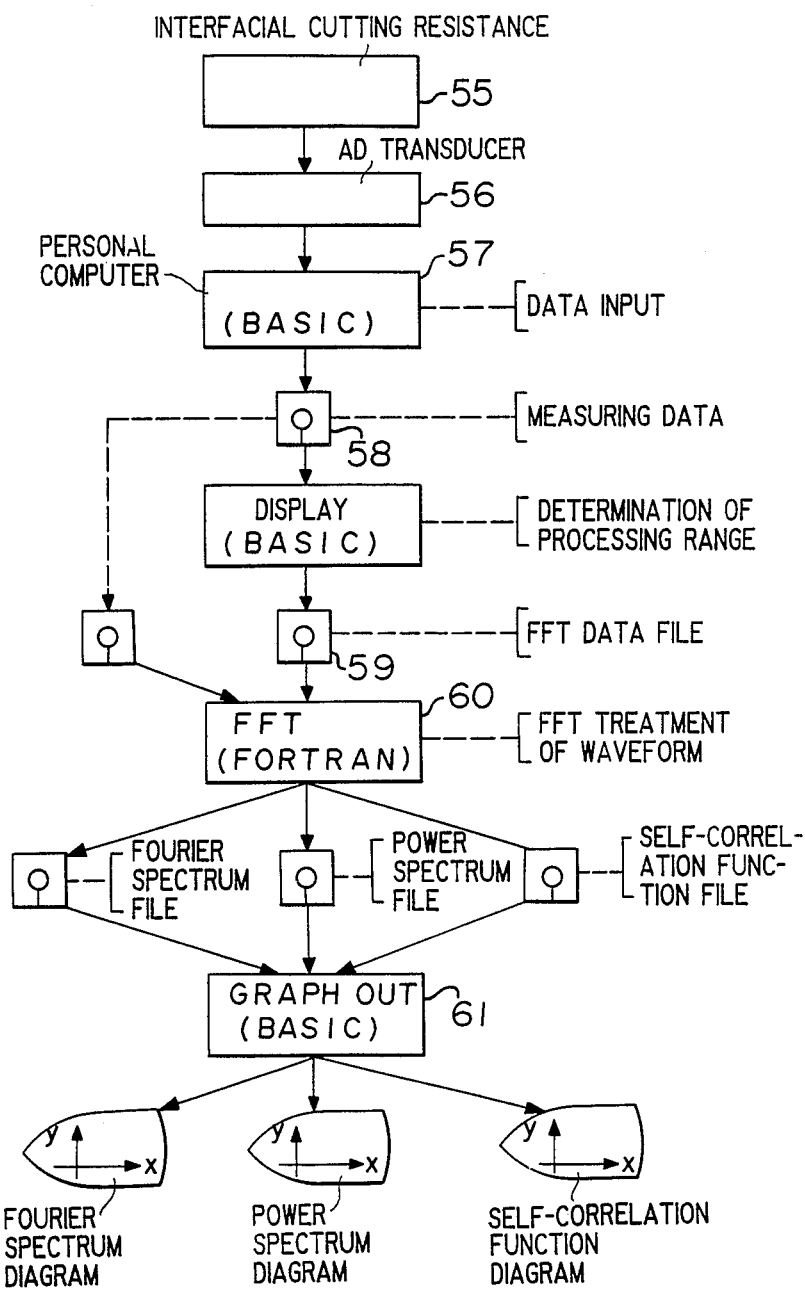
FIG. 15 is a flow chart of a waveform analysis program.
Figure 16:
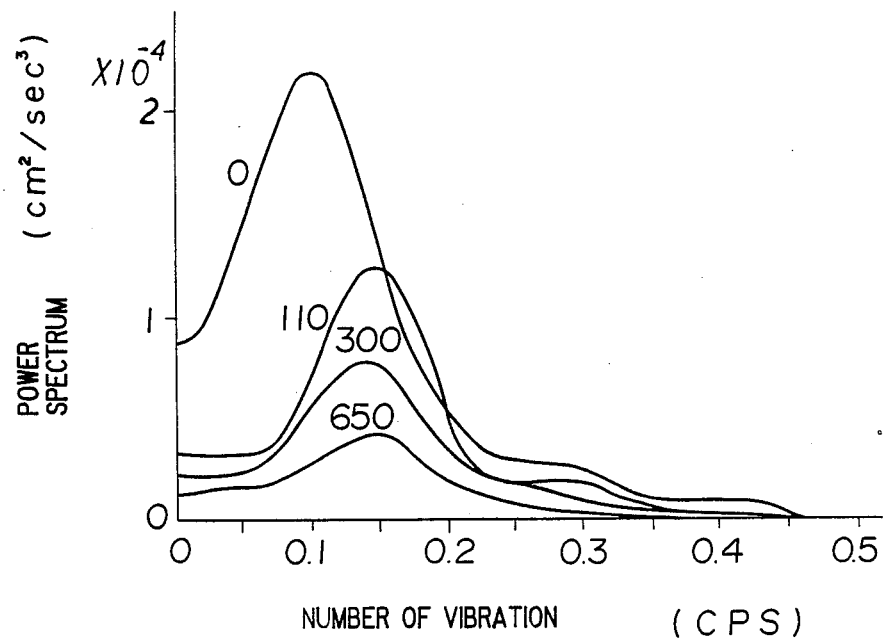
FIG. 16 is a graphical representation showing vibration frequency versus power spectrum characteristic curves obtained by the Fourier conversion of a urethane type coating material.

FIGS. 11(a) to 11(d) are respectively characteristic diagrams showing the results of measurement of the cutting resistance with the pressing load W of 1.7 kg applied to the cutting blade for measuring the adhesive strength and the shear strength of the interlayer of a four-layered coated film such as, for example, automobile paint coating. FIG. 11(a) denotes the result of measurement of a clear top coat (solid color) of melamine/alkyl type coating with a film thickness of 33 μm; FIG. 11(b) indicates the result of measurement of a top coat (metallic color) of melamine/alkyl type coating with a film thickness of 13 μm; FIG. 11(c) indicates the result of measurement of an intermediate coat of melamine/alkyl type coating with a film thickness of 39 μm; and FIG. 11(d) indicates the result of measurement of an undercoat of cationic electro-deposition type coating with a film thickness of 24 μm. In these graphs, the ordinate axis represents the cutting resistance (kg) and the abscissa axis denotes the moving time (min.) of the cutting blade. The undercoat has its shear strength of as high as 710 kg/cm$^2$, and its adhesive strength of 720 kg/cm$^2$ which is in the region of cohesive failure (which corresponds to the shear strength of the coated film, and the cutting blade is in a balanced position where the value of $F_T$ becomes substantially zero). The intermediate coat has its shear strength of 410 kg/cm$^2$ and its adhesive strength of 400 kg/cm$^2$ which is in the region of cohesive failure. The metallic coating has its shear strength of 690 kg/cm$^2$ and its adhesive strength of 710 kg/cm$^2$ which is in the region of cohesive failure. The clear coat has its shear strength of 370 kg/cm$^2$ and its adhesive strength is 330 kg/cm$^2$ which is in the region of interfacial failure. In this way, it is possible to sequentially measure the shear strength and the adhesive strength of a multi-layered coating starting from the surface layer to the under layers, and it is also possible to judge from the values of both properties as to whether the failure taken place is the cohesive failure or the interfacial failure. Thus, it becomes possible to measure the adhesive strength and the shear strength of each and every layer of the multi-layered coating in a simple operation and with high precision by means of the device for measuring the adhesive strength and the shear strength of the coated film according to the present invention.

Additionally, it is also possible to carry out processing of the data as stored in the external memory device (27) not at the working site, but in the laboratory by taking them back there.

As such, the device for measuring the shear strength and the adhesive strength according to the present invention can be mounted on any part and in any direction of the object to be measured (22) by use of the fixing member (24), so that the properties of the coated film can be measured directly at the working site with the consequent improvement in reliability and precision of the measured data.

Incidentally, in the above-described embodiment of the present invention, explanations have been given as to a case wherein the magnet is used as the fixing member (24). However, the present invention is not limited to the magnet along, but any other implements such as a clamping jig like an anvil, etc. may also by employed.

Further, in the above-described embodiment, explanations have been given as to a case wherein the cutting blade (15) is placed on the coated pate (22) by pushing it with the spring (29). Again, the present invention is not limited to the spring alone, but any other elastic means may be utilized. Furthermore, hydraulic devices, electromagnetic force, compressed air, and so on may be used.

For the cutting blade (15), there may be used cemented carbide bites, diamond bite, and so forth having, for example, the width of 4 cm, the blade angle of 70 degrees, the clearance angle of 10 degrees, and the rake angle of 10 degrees. For the pressure detector (4, 1), those which utilize a general strain gauge may be used. It may also be feasible to use an angular elastic ring (72), the construction of which is shown in the drawing. The motor (11) to be used may also be of general type. A stepping motor may also be utilized.

Furthermore, the bearing mechanism to be used is a combination of the guide shaft (2, 6, 14, 18, 71) and the sliding member (3, 5, 12, 13, 19) with the least play between them.

Moreover, in the above-described embodiment of the present invention, explanations have been given on the measuring device, in which the differential transducer (55) is provided as the vertical displacement detector for detecting the vertical displacement of the cutting blade (a displacement in the direction of depth of the coated film). Even if there is provided no vertical displacement detector, however, the adhesive strength and the shear strength can be found out, with the same effect, by detection of the cutting position of the blade (15) from an amount of expansion of a piezoelectric element.

As has so far been mentioned in the foregoing, the measuring device according to the present invention has the effect of being able to directly measure the adhesive strength or the shear strength of the coated film of the object to be measured, and to measure the adhesive strength or the shear strength of each and every layer in a multi-layered coating.

Also, the measuring device according to the present invention is able to detect the cutting resistance of the object to be measured, with simultaneous detection of the measuring position with the consequence that it is capable of effectively measuring the adhesive strength and the shear strength of the coated film in a simpler manner and with higher precision.

In the foregoing, the present invention has been described in specific details with reference to a preferred embodiment thereof as shown in the accompanying drawing. It should, however, be noted that the embodiment is merely illustrative of the invention, and no so restrictive, and that any changes and modifications may be made by those persons skilled in the art without departing from the spirit and scope of the present invention as recited in the appended claims.

What is claimed is:

1. A device for measuring adhesive strength or shear strength of a coated film, which comprises in combination:
   (a) a fixed member which can be fixed on an object to be measured;
   (b) a guide member fixed on said fixed member;
   (c) a moving member which moves linearly on and along said guide member in parallel with a measuring surface of said object to be measured;
   (d) a cutting blade supporting member which displaces linearly in parallel with the measuring surface of said object to be measured in association with said moving member and which is linearly displaceable in the direction perpendicular to said measuring surface;

(e) a cutting blade mounted on one end part of said cutting blade supporting member and press-contacted on said measuring surface by a predetermined force;

(f) means for adjusting the press-contacting force of said cutting blade onto said measuring surface, said adjusting means being disposed at the other end part of said cutting blade supporting member;

(g) means for adjusting a press-contacting angle of said cutting blade;

(h) a pressure detector for detecting cutting resistance to be generated in said cutting blade; and (i) means for recording an output from said pressure detector.

2. A measuring device according to claim 1, wherein said means for adjusting the press-contacting force of said cutting blade to said measuring surface is constructed with a screw-threaded rod integrally coupled with a guide shaft which brings about movement of said cutting blade, and adjusting screw with a control lug which is screw-connected with said screw-threaded rod, a sliding member slidably fitted on the upper part of said screw-threaded rod, and a spring member interposed between said adjusting screw and said sliding member.

3. A measuring device according to claim 2, wherein said sliding member is connected with a pressure detector which is mounted on the upper part of a pressure detector supporting table which, in turn, is fixed on said guide members.

4. A measuring device according to claim 1, wherein said means for adjusting the press-contacting angle of said cutting blade is provided with a sliding member which rotatably holds, on and around the central axis thereof, a supporting member for holding said cutting blade and a guide shaft integrally connected with said supporting member.

5. A device for measuring adhesive strength or shear strength of a coated film, which comprises in combination:

(a) a fixed member which can be fixed on an object to be measured;

(b) a guide member fixed on said fixed member;

(c) a moving member which moves linearly on and along said guide member in parallel with a measuring surface of said object to be measured;

(d) a cutting blade supporting member which displaces linearly in parallel with the measuring surface of said object to be measured in association with said moving member and which is linearly displaceable in the direction perpendicular to said measuring surface;

(e) a cutting blade mounted on one end part of said cutting blade supporting member and press-contacted on said measuring surface by a predetermined force;

(f) means for adjusting the press-contacting force of said cutting blade onto said measuring surface, said adjusting means being disposed at the other end part of said cutting blade supporting member;

(g) means for adjusting a press-contacting angle of said cutting blade;

(h) a vertical displacement detector for detecting a displaced quantity of said cutting blade in the direction vertical to the measuring surface of said object to be measured;

(i) a pressure detector for detecting cutting resistance to be generated in said cutting blade; and (j) means for recording outputs from said pressure detector and said vertical displacement detector.

6. A measuring device according to claim 5, wherein said means for adjusting the press-contacting force of said cutting blade to said measuring surface is constructed with a screw-threaded rod integrally coupled with a guide shaft which brings about movement of said cutting blade, and adjusting screw with a control lug which is screw-connected with said screw-threaded rod, a sliding member slidably fitted on the upper part of said screw-threaded rod, and a spring member interposed between said adjusting screw and said sliding member.

7. A measuring device according to claim 6, wherein said sliding member is connected with a pressure detector which is mounted on the upper part of a pressure detector supporting table which, in turn, is fixed on said guide members.

8. A measuring device according to claim 5, wherein said means for adjusting the press-contacting angle of said cutting blade is provided with a sliding member which rotatably holds, on and around the central axis thereof, a supporting member for holding said cutting blade and a guide shaft integrally connected with said supporting member.

* * * * *